United States Patent [19]

Judet

[11] 4,263,904
[45] Apr. 28, 1981

[54] OSTEOSYNTHESIS DEVICES

[76] Inventor: Robert L. Judet, 42, rue Bugeaud, 75016 Paris, France

[21] Appl. No.: 9,852

[22] Filed: Feb. 6, 1979

[30] Foreign Application Priority Data

Feb. 10, 1978 [FR] France ................. 78 03758

[51] Int. Cl.³ .............................................. A61F 5/04
[52] U.S. Cl. ............................... 128/92 B; 128/92 D; 128/92 G
[58] Field of Search ............. 128/92 B, 92 EA, 92 D, 128/83, 325, 337, 92 G

[56] References Cited

U.S. PATENT DOCUMENTS

| | | | |
|---|---|---|---|
| 1,156,440 | 10/1915 | Smith | 128/92 EA |
| 2,201,610 | 5/1940 | Dawson, Jr. | 128/337 |
| 2,494,792 | 1/1950 | Bloom | 128/92 EA |
| 2,966,907 | 1/1961 | Fasolino | 128/92 EA |
| 3,068,870 | 12/1962 | Levin | 128/337 |
| 3,469,573 | 9/1969 | Florio | 128/92 R |
| 3,807,394 | 4/1974 | Attenborough | 128/92 B |
| 3,824,995 | 7/1974 | Getscher et al. | 128/92 B |
| 3,939,828 | 2/1976 | Mohr et al. | 128/92 B |
| 3,988,783 | 11/1976 | Treace | 128/92 B |
| 4,119,091 | 10/1978 | Partridge | 128/92 B |
| 4,146,022 | 3/1979 | Johnson et al. | 128/92 B |

Primary Examiner—Robert W. Michell
Assistant Examiner—C. W. Shedd
Attorney, Agent, or Firm—Finnegan, Henderson, Farabow, Garrett & Dunner

[57] ABSTRACT

A device for holding together the parts of a fractured bone which has the shape of an open resilient bracelet and which contacts the bone only at several support points.

3 Claims, 12 Drawing Figures

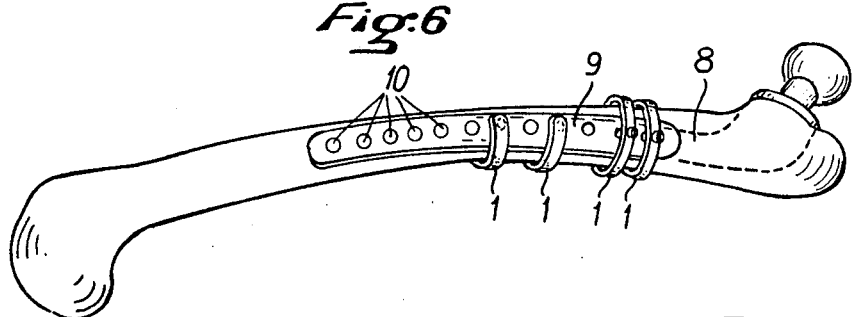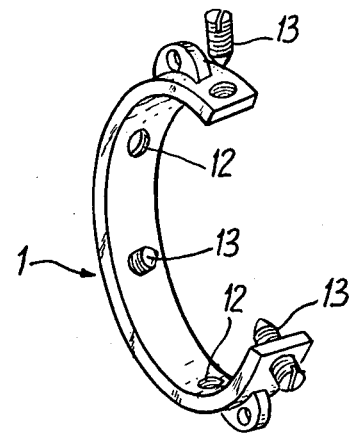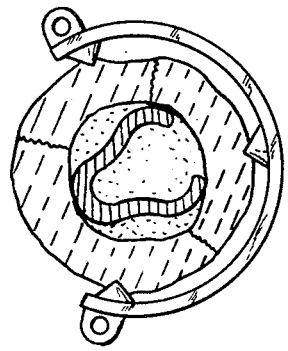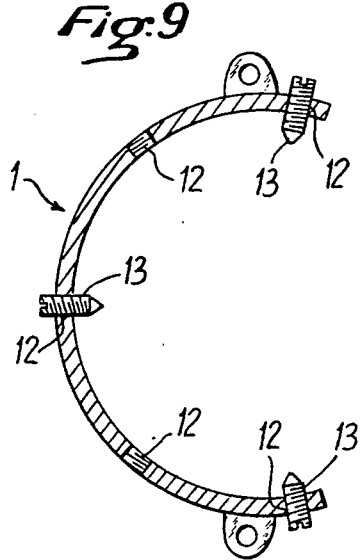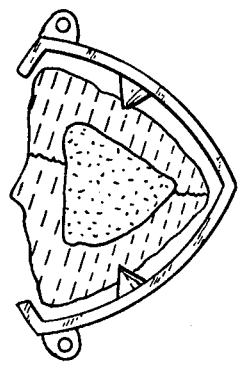

OSTEOSYNTHESIS DEVICES

BACKGROUND AND SUMMARY OF THE INVENTION

The present invention relates to an osteosynthesis device for providing fixation of oblique or spiroidal fractures or the fixation of lateral splinters through a ligature which is incomplete, non constrictive and with continuous resilient pressure.

When the bone is split into various fragments, it has been attempted to maintain the various fragments in place by means of ligatures with a thread of ligatures made with Parham type tapes. However, said ligatures which completely surround the bone are thereby constrictive, and their effect is to interrupt or gravely compromise the vascularization to a point that in such a case the bone thus squeezed breaks on the seat of the ligature.

On the other hand, when the medullary canal of a bone is occupied by a prosthesis or a nail, it is impossible to position a plate or to fix a fragment by positioning correctly a screw, that is by perforating the bone from cortical to cortical.

The device according to the present invention is characterized in that it is made of an open and resilient bracelet formed on it inner wall with several support points which contact the bone during use. Preferably, the number of said support points is three.

The invention will become more apparent from the following description of non limitative embodiments, reference being made to the accompanying drawings wherein:

BRIEF DESCRIPTION OF THE DRAWINGS

FIG. 6 is a perspective view showing an example of the positioning of the bracelet with a plate on a bone;

FIG. 7 is a partial cross-sectional schematic view showing an example of the positioning of the bracelet on a nailed bone;

FIG. 8 is a perspective view of an alternative embodiment,

FIG. 9 is a cross-sectional view of the device of FIG. 8;

FIG. 10 is a partial cross-sectional schematic view of a further embodiment of the invention.

DETAILED DESCRIPTION OF THE PREFERRED EMBODIMENTS

Figure 1:
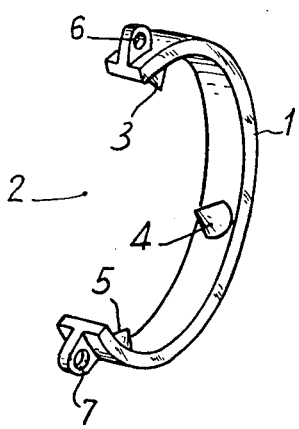
FIG. 1 is a perspective view of an embodiment of the device of the invention.

Referring to FIG. 1, the device is a circular bracelet 1 formed with an opening over an angle slightly superior to 90°. The inner wall of the bracelet comprises three bosses 3, 4 and 5 which are pointed and form preferably an apex angle of 90°. As is shown in the figure, bosses 3 and 5 are positioned at the two ends of bracelet 1, boss 4 being in the center.

Each of the outer walls of the bracelet is respectively formed at its ends with a perforated wing 6 or 7.

Figure 2:
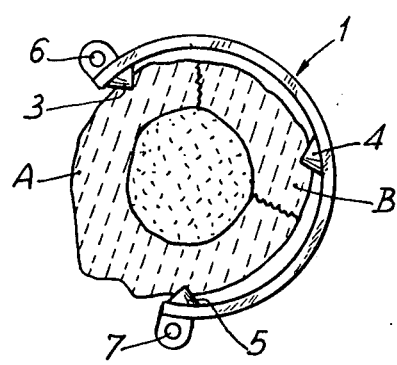
FIGS. 2 and 3 are partly sectional schematic views showing two examples of the positioning of the bracelet on a bone.
Figure 3:
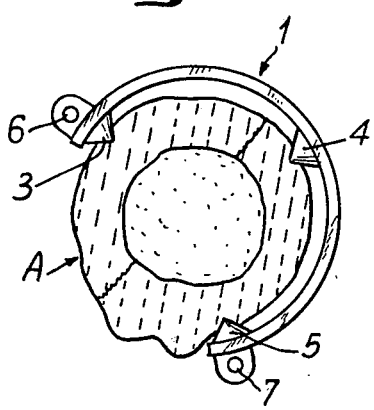

FIGS. 2 and 3 show the manner in which the open bracelet 1 is used. The splinter B is maintained pressed onto the bone A through the support applied by point A, bracelet 1 being anchored through bosses 3 and 5 onto the bone. In FIG. 3, the bone is broken practically in its middle portion, boss 3 being engaged on one portion and bosses 4 and 5 on the other portion.

Figure 4:
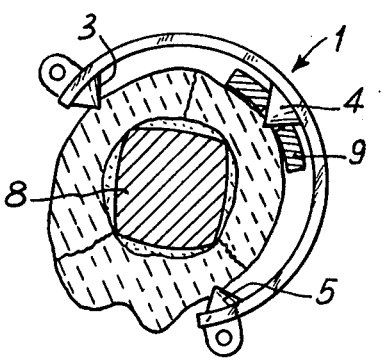
FIGS. 4 and 5 are two partial cross-sectional schematic views showing two examples of the positioning of the bracelet on a bone, in combination with a plate.

The bracelet may also be used for fixating a plate. Normally, a plate has to be screwed by a screw extending completely through the bone from cortical to cortical and through the medullar canal. But, as is shown in FIG. 4, it may happen that the medullary canal is obstructed by a nail such as at 8. In thus case, one of the bosses, such as boss 4, may be introduced into the holes provided in the plate and plate 9 is maintained in place on the bracelet. Generally, the plate screw holes are formed with a countersinking with an apex angle of 90° so that the boss may perfectly fit into the hole. Preferably, the depth of the the screw head countersinking is determined such that the boss 4 point may be in contact with the bone.

Figure 5:
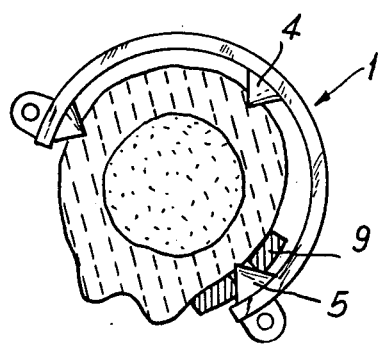

FIG. 5 shows an alternative use of the bracelet 1 for maintaining a plate 9 according to which plate 9 is maintained by an end boss of the bracelet.

FIG. 6 shows the use of several bracelets for maintaining a plate 9 along a femur provided with a prosthesis of the femur head comprising a nail 8 driven into the medullar canal.

Plate 9 is screwed by screws 10 in the inner portion of the bone and is maintained by bracelet 1 positioned either astride as is shown in FIG. 4 or by providing a lateral squeeze as is shown in FIG. 5.

FIG. 7 shows a further example of the use of the bracelet 1 on a multi-fragment fracture nailed by means of a slit nail.

FIGS. 8 and 9 show an alternative of the embodiment, according to which the bracelet 1 is formed with a plurality of tapped holes 12 in which the threaded bosses 13 can be engaged and the depth of which can be set, the length of each boss protruding inside the bracelet. Moreover, as there are more than three tapered openings 12, it is possible to vary the position of bosses 13.

The bracelet thus described is not circular and touches the bone only in three points. The result is that it can be perfectly adapted to any bone, whatever the irregularities of the contour of the latter.

Moreover, since only the points of the bosses are in contact with the cortical of the bone, or of the fragment splinters, whereas the body as such of the bracelet is out of contact, there is no constriction effect as is the case with the known devices.

Since the bracelet is put in position through resilient deformation, it acts like a spring and applies a constant pressure.

Further, it is always very easy to take away since it cannot be trapped into the bone mass.

FIG. 10 shows an alternative embodiment wherein the bracelet is triangular in shape whereby it can be adapted to the very particular shape of the tibia.

Figure 11:
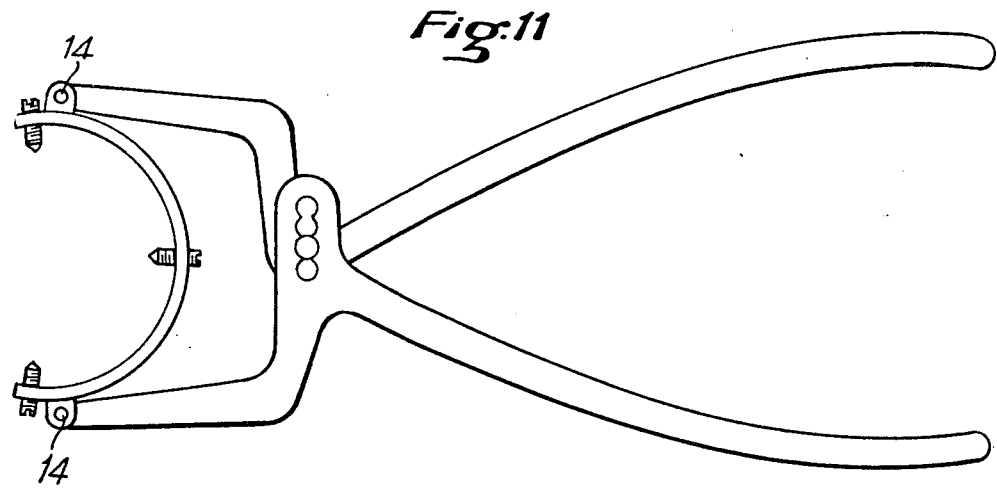
FIG. 11 is a schematic view of clamps used for the frontal positioning of a bracelet according to the invention.
Figure 12:
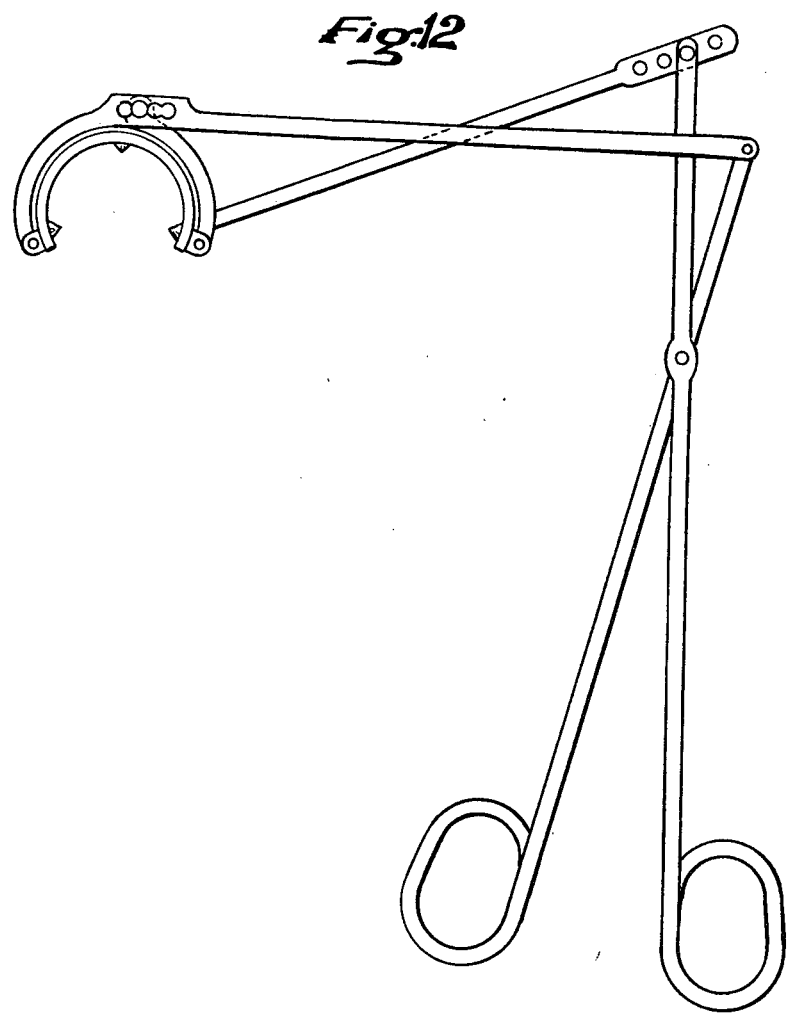
FIG. 12 is a schematic view of a clamp provided for the lateral positioning of a bracelet according to the invention.

The bracelet is put in position by means of a spreading clamp, the branches of which are provided at their ends with protrusions 14 engaging the perforated wings 6 and 7; such a clamp may be straight as is shown in FIG. 11, or angled as is shown in FIG. 12.

I claim:

1. A device for the fixation of a fractured bone comprising a one-piece bracelet having an inner wall and an outer wall and having free ends forming an opening in said bracelet, the bracelet having spring-like resilience and including at least two support points spaced along its inner wall, said support points anchoring the bracelet to said fractured bone and holding the portions of fractured bone in the a fixed relative position relative to each other by means of only said spring-like resilience of the bracelet.

2. The device according to claim 1, includes three support points.

3. The device according to claims 2, or 1 wherein said bracelet has a perforated wing on the outer wall formed at each free end, said two perforated wings providing spreading means for the engagement and disengagement of said device about said fractured bone.